United States Patent [19]
Gemma, Jr. et al.

[11] Patent Number: 5,988,367
[45] Date of Patent: Nov. 23, 1999

[54] UNIVERSAL SUTURE DISPENSER BOX

[75] Inventors: Edward A. Gemma, Jr., Milford; David Viselli, Shelton; John S. Scott, Bristol; William T. Mitchell, III, Guilford, all of Conn.

[73] Assignee: United States Surgical Corporation, Norwalk, Conn.

[21] Appl. No.: 08/854,823

[22] Filed: May 12, 1997

Related U.S. Application Data

[63] Continuation-in-part of application No. 08/690,947, Jul. 16, 1996, Pat. No. 5,860,517.

[51] Int. Cl.[6] .............................. A61B 17/06; B65D 5/72
[52] U.S. Cl. ........................ 206/63.3; 206/499; 221/305; 229/122.1
[58] Field of Search .................................. 206/63.3, 499, 206/738, 776–778, 781–783; 229/122, 122.1, 162; 221/305, 306; 211/197, 266, 281, 256

[56] References Cited

U.S. PATENT DOCUMENTS

| | | |
|---|---|---|
| D. 221,427 | 8/1971 | Savettiere et al. . |
| D. 224,692 | 8/1972 | Gray . |
| D. 232,677 | 9/1974 | Schotland . |
| D. 260,955 | 9/1981 | Schuler et al. . |
| 902,347 | 10/1908 | Tillinghast . |
| 1,119,213 | 12/1914 | Abt . |
| 1,823,572 | 9/1931 | Reed . |
| 1,973,237 | 9/1934 | Vilas . |
| 1,986,101 | 1/1935 | Brodsky . |
| 2,002,485 | 5/1935 | Alfred . |
| 2,005,924 | 6/1935 | Wilson . |
| 2,577,862 | 12/1951 | Shaw, Jr. . |
| 2,755,922 | 7/1956 | Volckening . |
| 2,767,832 | 10/1956 | Silberman . |
| 2,785,843 | 3/1957 | Shaw ..................................... 229/122.1 |
| 3,014,634 | 12/1961 | Humphrey et al. . |
| 3,156,378 | 11/1964 | Bua . |
| 3,160,342 | 12/1964 | Murdock et al. . |
| 3,356,279 | 12/1967 | Root . |
| 3,450,308 | 6/1969 | Schoenefeld ............................. 221/305 |
| 3,568,883 | 3/1971 | Reynolds . |
| 3,580,472 | 5/1971 | Stawski . |
| 3,586,206 | 6/1971 | Gilmore et al. . |
| 4,148,413 | 4/1979 | Immordino . |
| 4,170,325 | 10/1979 | Pawlowski et al. . |
| 4,186,866 | 2/1980 | Zicko . |
| 4,215,777 | 8/1980 | Strickland . |
| 4,396,143 | 8/1983 | Killy . |
| 4,405,044 | 9/1983 | Flower et al. . |
| 4,458,814 | 7/1984 | Meschi . |
| 4,497,432 | 2/1985 | Milia . |
| 4,566,607 | 1/1986 | Smith . |
| 5,249,737 | 10/1993 | Fritz et al. ........................... 229/122.1 |
| 5,282,533 | 2/1994 | Holzwarth et al. . |
| 5,284,293 | 2/1994 | Alpern et al. . |
| 5,328,082 | 7/1994 | Fritz et al. ........................... 229/122.1 |
| 5,458,272 | 10/1995 | Ward-Weber . |
| 5,542,539 | 8/1996 | Early . |

FOREIGN PATENT DOCUMENTS 2458480  2/1981  France .

*Primary Examiner*—Bryon P. Gehman

[57] ABSTRACT

A dispenser box for suture packages includes an outer casing and drawer portion slidably disposed within the outer casing. The dispenser preferably includes at least two access portals for withdrawal of the suture packages. A first access portal allows the suture packages to be withdrawn in accordance with the U.S. preferred mode, wherein the dispenser box disposed so that the suture packages are stacked in a vertical array and withdrawn horizontally. A second access portal allows the suture packages to be withdrawn in accordance with the European preferred mode, wherein the suture packages are stacked in a horizontal array and are withdrawn vertically.

21 Claims, 9 Drawing Sheets

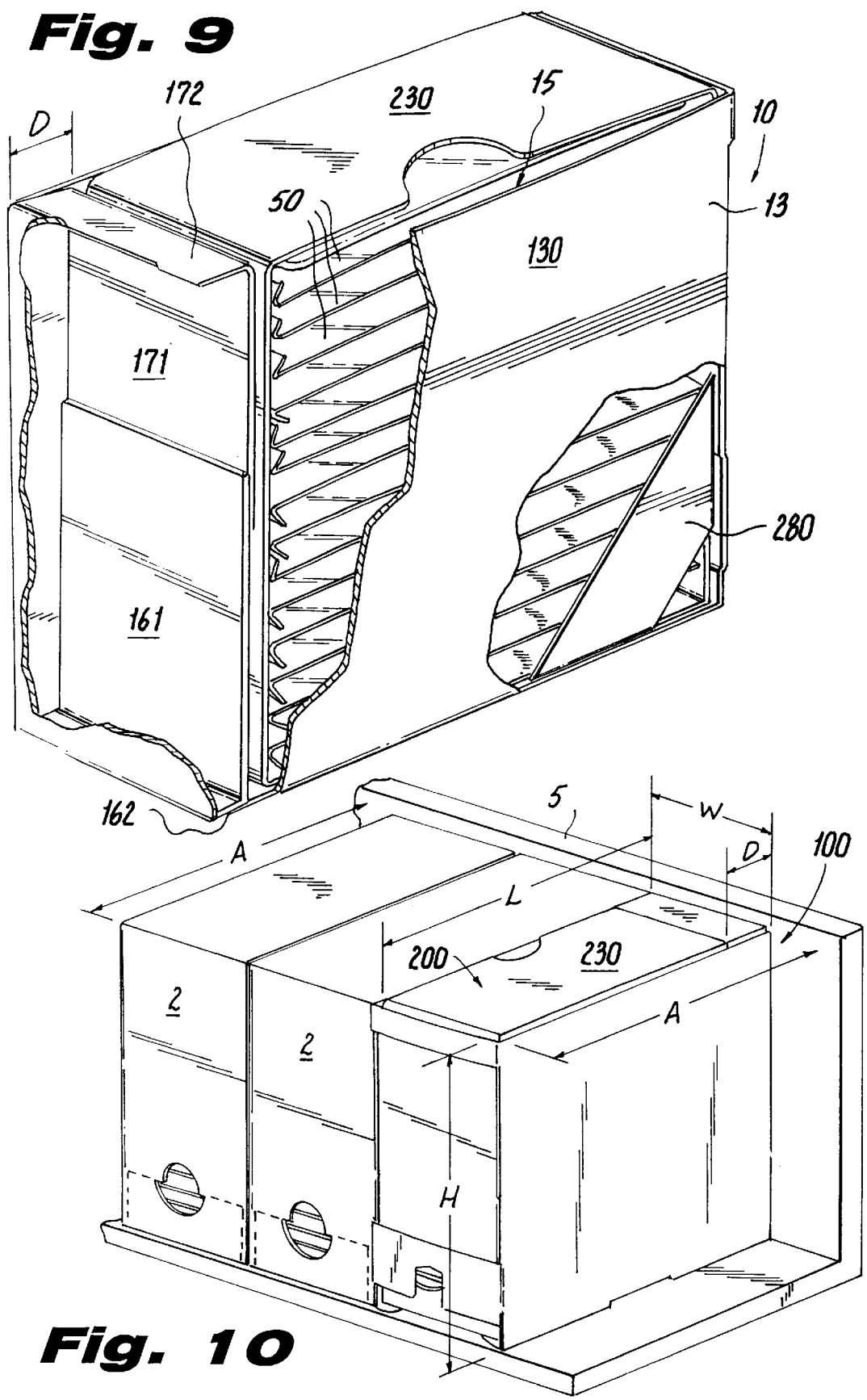

UNIVERSAL SUTURE DISPENSER BOX

CROSS-REFERENCE TO RELATED APPLICATIONS

This application is a continuation-in-part of U.S. application Ser. No. 08/690,947, filed Jul. 16, 1996, in which U.S. Pat. No. 5,860,517 issued on Jan. 19, 1999.

BACKGROUND

1. Technical Field

The container disclosed herein relates to a dispensing box for packaged surgical sutures. More specifically, the suture dispensing box is configured to be used in both the U.S. preferred mode wherein the box is vertically disposed, and in the European preferred mode, wherein the box or a portion thereof is disposed horizontally.

2. Background of the Art

Modern surgical procedures draw upon a wide variety of types and sizes of surgical sutures. These sutures are usually contained in individual retainers or foil laminate envelopes wherein the suture is wound, for example, in a figure eight type pattern, or coil. Indicia indicating the size and type of the suture are typically printed on the enclosure envelopes to facilitate identification.

Dispensing boxes for such suture packages are known in the art. As shown in FIG. 1, the preferred format for dispensing boxes in the United States is to have the longer side of the box 2 disposed vertically. Suture packages 50 are retrieved horizontally from the bottom of the vertical stack of suture packages by grasping a shorter side of the generally rectangular suture package. As suture packages are withdrawn, the stack drops down to reposition other packages for retrieval.

The preferred European format, however, is with the longer side of the dispenser 2a and the stack of suture packages 50 disposed horizontally, as shown in FIG. 2. The dispenser 2a acts like a drawer, the suture packages being withdrawn vertically from the dispensing box 2a by grasping the longer side of the generally rectangular suture package. A typical operating room has suture box shelving or racks configured to accommodate either the U.S. or European boxes.

Because the U.S. and European dispensing boxes have different configurations, manufacturers currently provide separate boxes for each market. As such, two separate manufacturing, labeling and inventory systems must be maintained. What is needed is a dispensing box that can be used in both the U.S. preferred mode and the European preferred mode. Such a universal dispenser would eliminate the need for separate box constructions for different markets, providing both economy of manufacture and flexibility of use.

SUMMARY

A universal suture dispenser is provided herein. The universal suture dispenser is a container for holding a plurality of suture packages in a stacked array. The container includes an outer casing defining an interior space, and a drawer portion removably inserted into the interior space of the outer casing, the drawer portion having a floor and four panels defining a suture package storage compartment, the drawer portion having a support strip extending catercornered between two adjacent panels of the four panels.

In a preferred embodiment, the container has first and second adjacent sides, the suture packages being individually oriented perpendicular to the first side and parallel to the second side. The container has first and second access portals for withdrawal of the suture packages from the stacked array. The first access portal permits the suture packages to be withdrawn from the container in a line of direction perpendicular to the first side and parallel to the second side. The second access portal permits the sutures to be withdrawn from the container in a line of direction parallel to both the first and second sides. In a most preferred embodiment, the universal suture package dispenser includes an outer casing and a drawer portion slidably disposed within the outer casing. The drawer portion has a storage space for holding the stacked array of suture packages and a reinforcement strip extending across two adjacent panels.

The outer casing includes a first wall, a second wall foldably connected to the first wall along an edge thereof, a third wall foldably connected to the second wall on an edge of the second wall opposite to the edge at which the first wall is foldably connected, a fourth wall foldably connected to the third wall along an edge of the third wall opposite to that at which the second wall is connected, and a fifth wall foldably connected to the third wall, the aforementioned walls forming at least a partial enclosure defining an interior space and having an open end. The drawer portion includes first, second, third, fourth, fifth, sixth, and seventh panels, the second and third panels being foldably connected to the first panel along adjacent edges thereof, the fourth panel being foldably connected to the third panel along an edge of the third panel opposite to the edge at which the first panel is foldably connected, the fifth and sixth panels being foldably connected to the fourth panel along adjacent edges of the fourth panel, and the fourth and seventh panels being foldably connected to the sixth panel along respective adjacent edges of the sixth panel. The sixth and third panels are foldably connected to opposite edges of the fourth panel. The reinforcement strip preferably extends from the fourth panel to the sixth panel.

The universal suture package dispenser may be positioned vertically for dispensing suture packages in the U.S. preferred mode, or horizontally wherein the suture packages may be withdrawn in the European preferred mode. Optionally, a spacer panel may be included to conform the dimensions to those of conventional dispensers.

DETAILED DESCRIPTION OF THE DRAWINGS

FIG. 9 is a partially cut away perspective view of the universal suture package dispenser box wherein the suture packages are stacked vertically.

FIG. 10 is a perspective view showing the embodiment of FIG. 9 stacked with conventional suture package dispenser boxes.

DETAILED DESCRIPTION OF PREFERRED EMBODIMENTS

Figure 3:
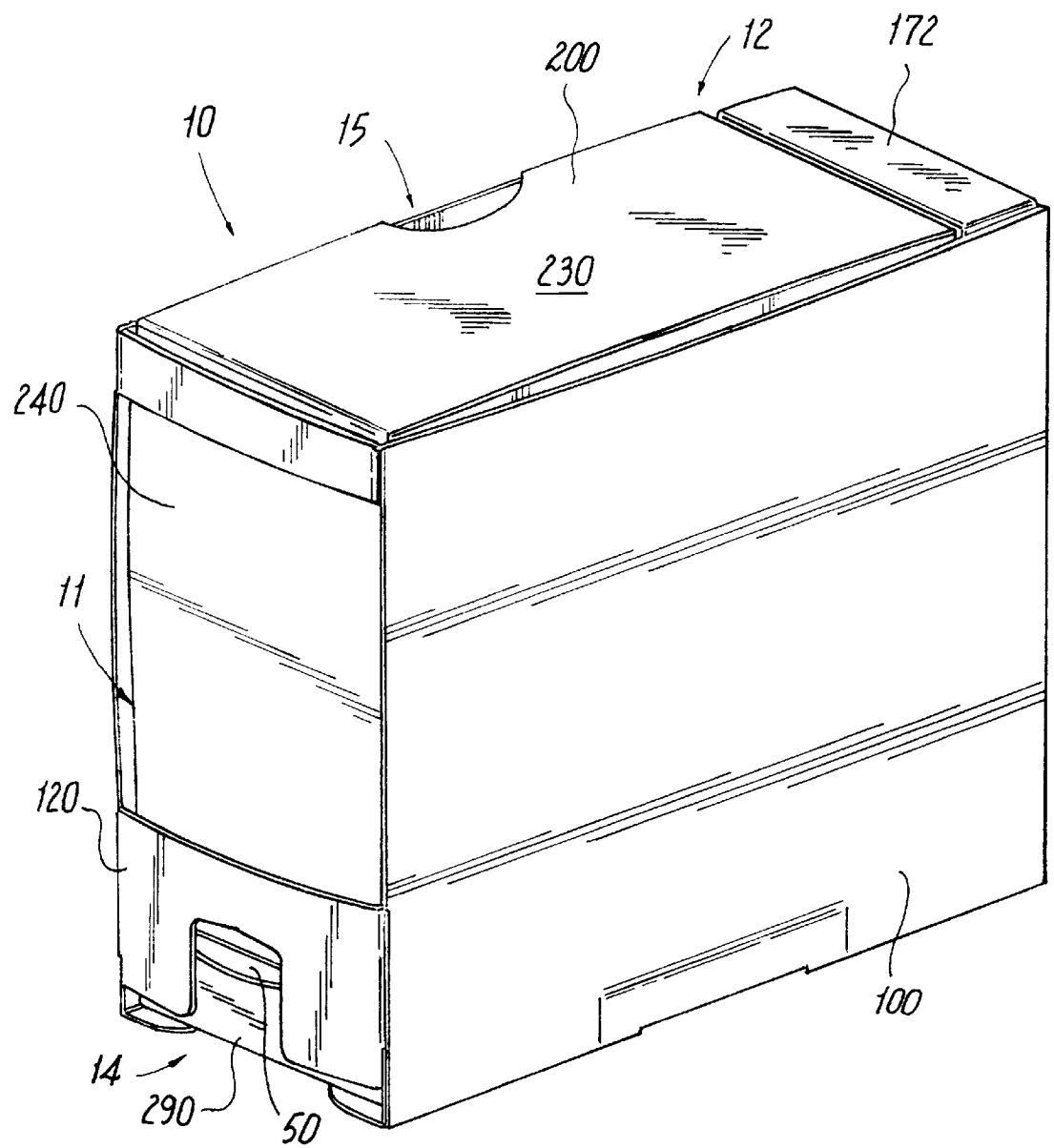
FIG. 3 is a perspective view of the universal dispenser box described herein positioned in a vertical orientation.
Figure 4:
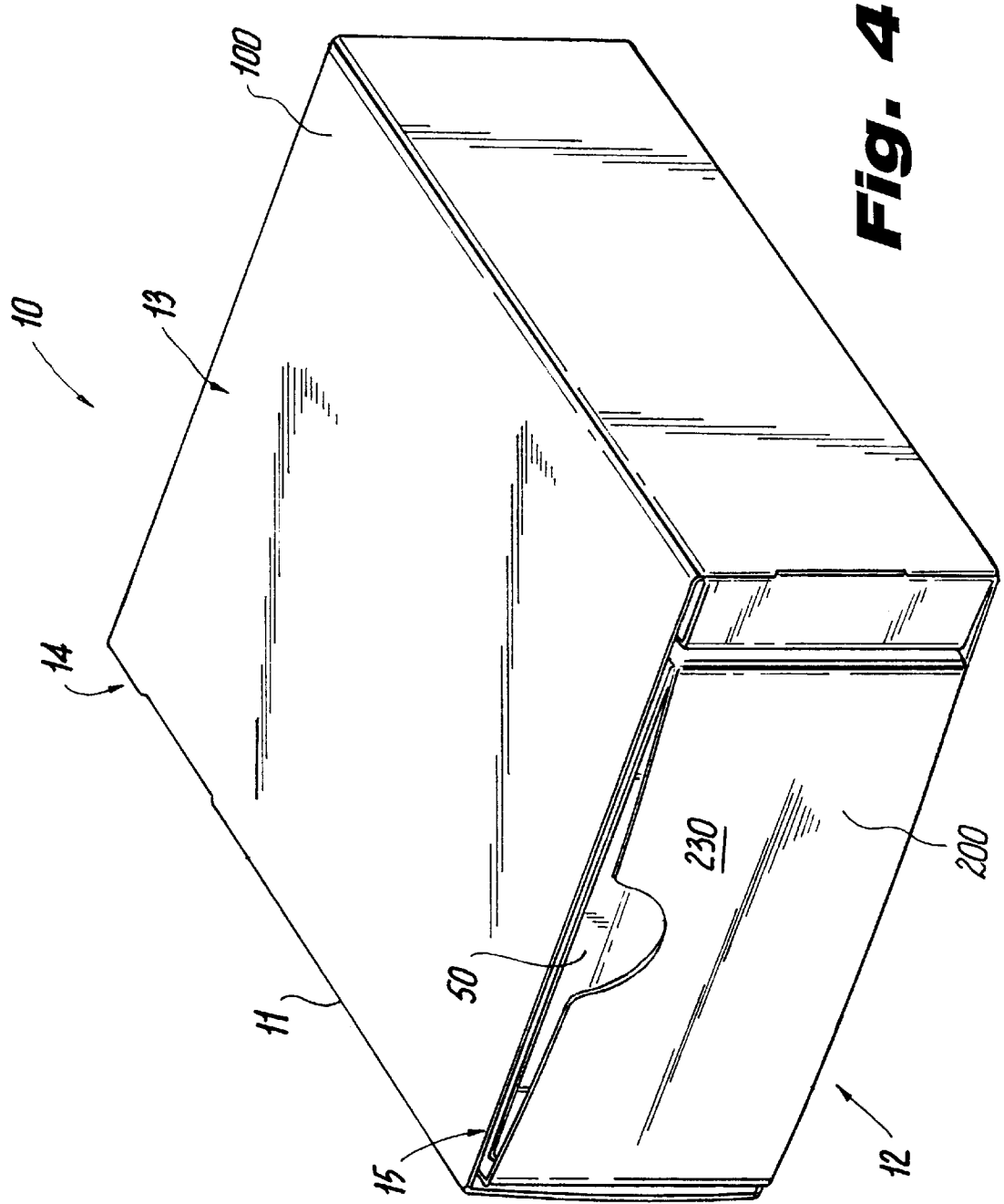
FIG. 4 is a perspective view of the universal dispenser box positioned in a horizontal orientation.

With reference to FIG. 3–4, a preferred universal suture dispenser 10 is described herein. Universal suture dispenser 10 includes an outer casing 100 having a folded blank defining an interior space, and a drawer portion 200 slidably disposed within the interior space of the outer casing. Individual suture packages are preferably stacked in a single array within the drawer portion. The suture packages are typically of a rectangular, planar configuration and are stacked such that the planes are parallel to each other. The stack can be positioned vertically, as in FIG. 3, or horizontally, as in FIG. 4. The suture dispenser can be fabricated from paperboard, cardboard stock, plastic sheet material or other material suitable for the purposes described herein.

Referring now to FIG. 3, universal suture dispenser 10 is illustrated in a vertical position as favored in the United States. In this position the planes of the individual suture packages are each horizontally oriented, but stacked vertically, one on top of the other. FIG. 4 illustrates the universal suture dispenser 10 positioned in the European preferred horizontal orientation. In this position the planes of the individual suture packages are vertically oriented, but stacked horizontally, one package being next to the other. In both positions as shown in FIGS. 3 and 4, the planes of the suture packages are parallel to each other.

Figure 5:
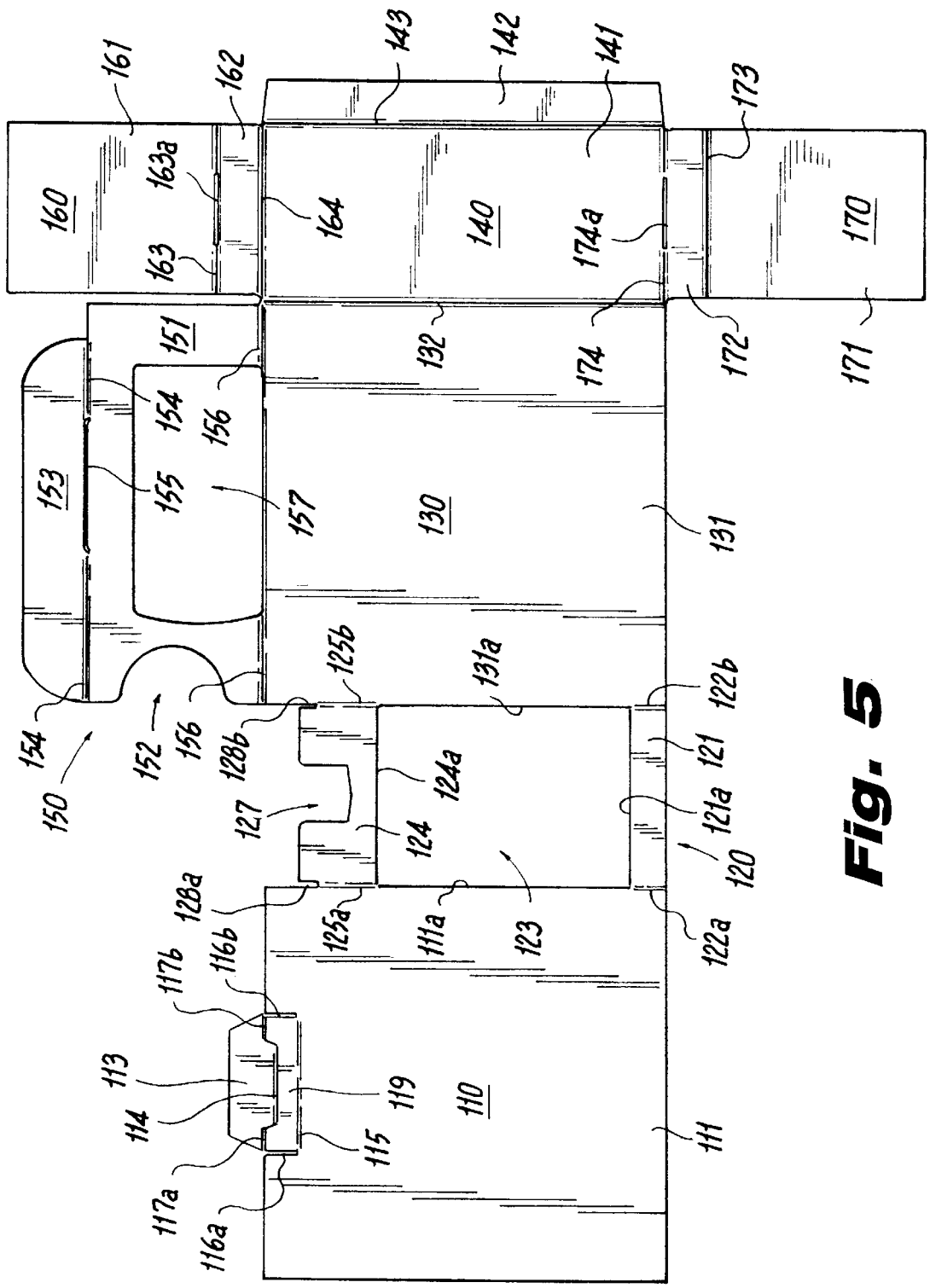
FIG. 5 is a plan view of the blank used to make the outer case of the universal dispenser box.

Referring now to FIG. 5, the blank from which the outer casing 100 is made is shown unfolded. Both the outer casing 100 and drawer portion 200 (FIG. 7) are formed from blanks having flat portions connected to each other along fold lines to form a sheet, or blank, which is folded to construct the outer casing or drawer portion. The main flat portions of the outer casing 100 will be referred to herein as "walls" and the main flat portions of the drawer portion 200 will be referred to herein as "panels." The outer casing blank has five main walls which correspond to exterior sides of the outer casing, and spacer walls to adapt the interior dimensions of the enclosed space to fit the drawer portion 200. Each of the walls is a flat sheet of suitable material such as mentioned above.

Wall 110 has a body portion 111 and tab 113. Tab 113 is adapted for insertion into slot 155 (discussed below) and is attached to bendable portion 119 along fold line 114. Bendable portion 119 is at least partially defined by slots 116a and 116b, and is attached to body portion 111 along fold line 115. Slots 117a and 117b between tab 113 and bendable portion 119 facilitate the bending of tab 113 relative to the bendable portion 119 and help to prevent inadvertent withdrawal of tab 113 from slot 155 after they have been fully engaged.

Wall 120 includes a first strip portion 121 extending between walls 110 and 130 and which is foldably connected thereto along fold lines 122a and 122b, respectively. A second strip portion 124 extends between walls 110 and 130 and is foldably connected thereto along fold lines 125a and 125b. Edges 111a of the wall 110, 131a of wall 130, 124a of second strip portion 124, and 121a of first strip portion 121 define a window opening 123. Window 123 enables the operating room personnel or other user to see identifying indicia printed on the outer side of panel 240 of the drawer portion 200 when the dispenser 10 is assembled. Finger slot 127 provides access to grasp the suture package with one's fingers (usually forefinger and thumb).

Wall 130 includes a body portion 131 attached to first and second strip portions 121 and 124 along fold lines 122b and 125b, respectively, and further is attached to wall 140 along fold line 132.

Wall 140 includes a body portion 141 to which flap 142 is attached along fold line 143.

Wall 150 includes a body portion 151 attached to wall 130 along fold line 156 and also includes a window 157 for permitting the operating room personnel or other user to read identifying indicia on the outer surface of wall 220 of the drawer portion 200. Edge 157a is preferably arcuate to facilitate removal and insertion of the drawer portion 200 into the assembled outer casing 100.

Wall 150 also preferably includes an arcuate cutout portion 152 to facilitate grasping of the suture package for withdrawal. Tab 153 is bendably attached to body portion 151 along fold line 154. Slot 155 is disposed along fold line 154 and is adapted to receive tab 113 of the first wall 110 when the walls are folded together to form the outer casing.

Spacer wall 160 includes a body portion 161 and a spacer portion 162 which is attached to body portion 161 along fold line 163. Fold line 163 can include a slit 163a extending partially across the fold line. Spacer portion 162 is attached to one edge of body portion 141 along fold line 164.

Spacer wall 170 includes a body portion 171 and a spacer portion 172 which is attached to body portion 171 along fold line 173. Spacer portion 172 is attached to an edge of the body portion 141 along fold line 174. Fold line 174 can include a slit 174a extending partially across the fold line.

Figure 6:
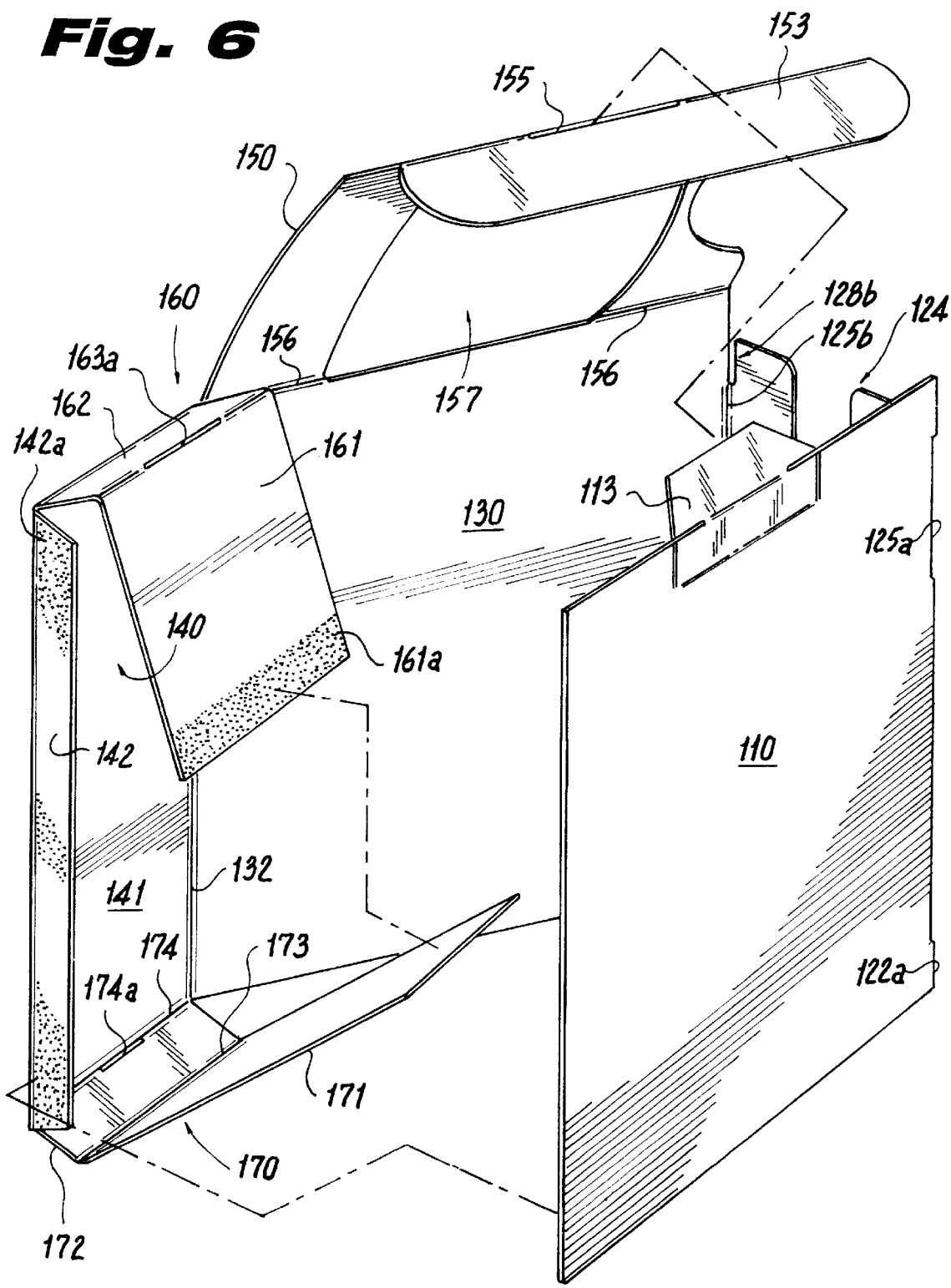
FIG. 6 is a perspective view illustrating the folding and assembly of the blank of FIG. 5 to form the outer case.

Referring now to FIG. 6, the folding operation is illustrated. Walls 110, 120, 130, 140, and 150 are folded inward along fold lines 122a, 125a, 122b, 125b, 132, and 156 to form a box-like structure. Flap 142 includes a gummed adhesive surface 142a adapted to abut an inner surface portion of first wall 110 and to adhere thereto. Wall 150 is folded with tab 153 tucked inside wall 110 with tab 113 being inserted through slot 155 to lock the walls and secure the enclosure. The spacer walls 160 and 170 are folded along fold lines 163, 164, 173, and 174 to construct an interior wall (formed by body portions 161 and 171) parallel to and spaced apart from body portion 141 by a distance equal to the width of spacer portions 162 and 172. Body portion 161 can have a gummed surface portion 161a to adhere to body portion 171. The outer casing thus formed is prepared to receive the drawer portion 200.

Drawer portion 200 is adapted to provide a storage space in which the suture packages are stacked. It is adapted to slidably fit within the interior space of outer casing 100. Alternatively, drawer portion 200 can be removed from outer casing 100 and can be stacked separately on a shelf.

Figure 7:
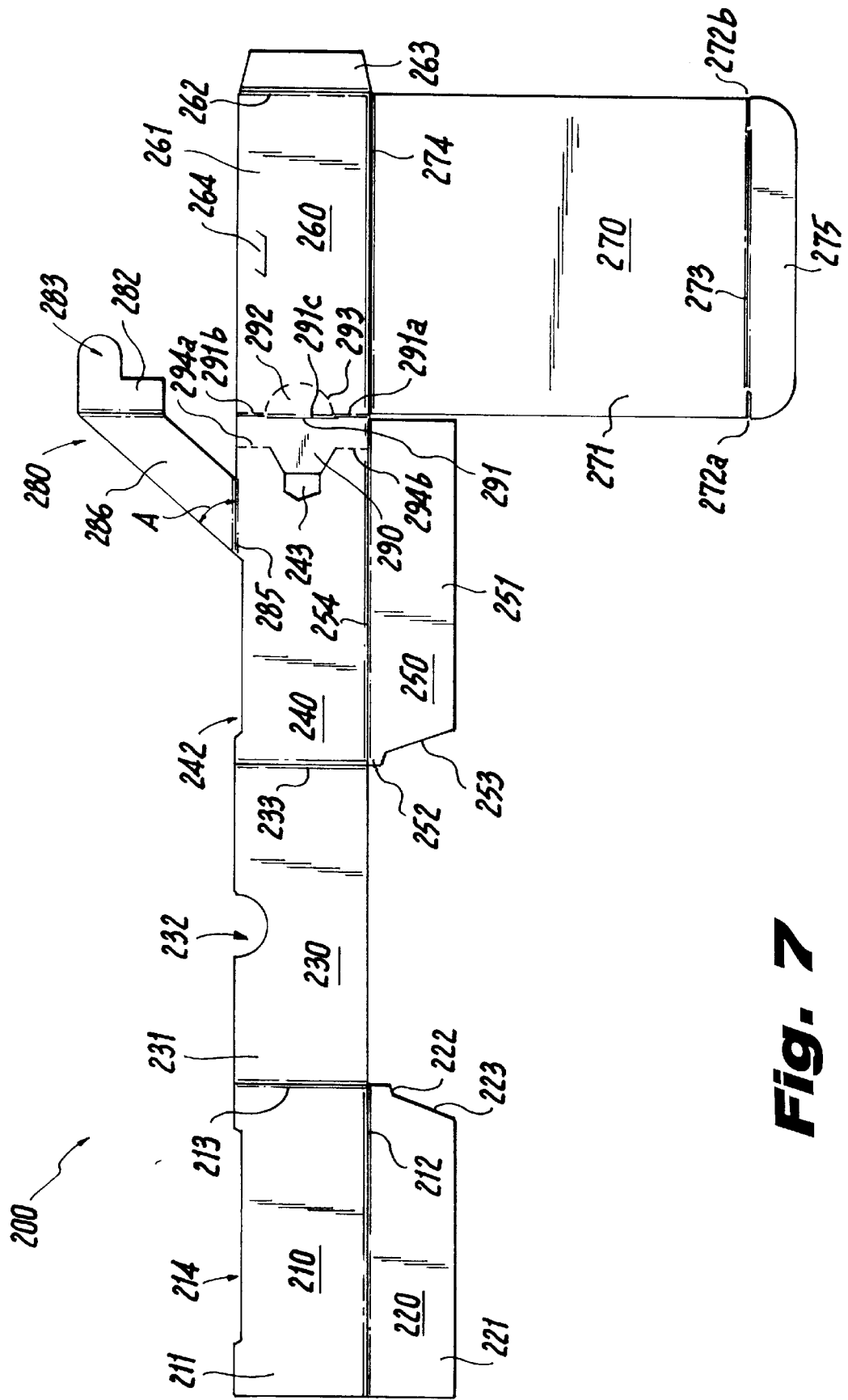
FIG. 7 is a plan view of a blank used to make the drawer portion of the dispenser box.

Referring to FIG. 7 as seen in unfolded plan view, the blank from which the draw portion 200 is folded includes several foldably connected panels.

First panel 210 includes a generally rectangular body portion 211 connected at fold line 212 to body portion 221 of second panel 220, and to body portion 231 of panel 230 at fold line 213. Fold lines 212 and 213 are adjacent and at a substantially right angle to each other. First panel 210 also includes an elongated recess 214 along an outer edge of body portion 211 opposite fold line 212.

Second panel 220 includes a body portion 221 connected to first panel 210 along fold line 212. Body portion 221 includes an angled side 223 with a laterally offset portion 222 for engaging slit 272b of the seventh panel 270 when the drawer portion 200 is foldably assembled. The inner surface of offset portion 222 provides an abutment which prevents tab 275 from inadvertently being withdrawn from a folded engagement configuration.

Third panel 230 includes a body portion 231 foldably connected to body portion 211 of first panel 210 at fold line 213; and to body portion 241 of fourth panel 240 at fold line 233. Third panel 230 also includes an arcuate cut away portion 232 along an edge of body portion 231 to provide access to the user's finger to grasp and pull the drawer portion 200.

Fourth panel 240 includes body portion 241 which is attached to body portion 231 at fold line 233, and to body portion 251 of fifth panel 250 at fold line 254. Fourth panel 240 includes an elongated recess 242 along the edge of body portion 241 opposite fold line 254. Recesses 242 and 214 provide elongated windows when the drawer portion 200 and outer casing 100 are assembled to permit the user to visualize the quantity of suture packages remaining in the dispenser box.

Fifth panel 250 includes a body portion 251 attached to the fourth panel 240 at fold line 254. Body portion 251 includes an angled side 253 with a laterally offset portion 252 for engaging slit 272a of the seventh panel 270 when the drawer portion 200 is foldably assembled. The inner surface of offset portion 252 provides an abutment which prevents tab 275 from inadvertently being withdrawn from a folded engagement configuration.

Removable retainer piece 290 is attached to body portion 241 at score lines 294a and 294b which have perforation to facilitate tearing and forms part of panels 240 and 260, fold line 291 demarcating the fourth and sixth panels 240 and 260, respectively. Retainer piece 290 includes an arcuate tab 292 which is foldably connected to the rest of the retainer piece 290 at fold line 291, which has a central unperforated portion 291c and two scored end portions 291a and 291b. Arcuate tab is at least partially defined by arcuate score line 293 which connects to the scored end portions 291a and 291b of fold line 291. An edge of body portion 241 and the removable piece 290 define an open space 243 therebetween. Removable piece 290 is adapted to be detached from the drawer portion 200 by ripping along score lines 294a, 294b, and 293, to provide a means of access to the suture packages stored in the dispenser box drawer portion 200 after the dispenser box is assembled.

Sixth panel 260 includes a body portion 261 having a slit 264 adapted to receive insertion portion 283 of tab 282, as discussed below. Body portion is connected to flap 263 at fold line 262, and to seventh panel 270 at fold line 274. Flap 263 is bonded to the inside surface (when folded) of body portion 211 by adhesion or other suitable method.

Seventh panel 270 includes a body portion 271 attached to body portion 261 at fold line 274, and to flap 275 at fold line 273. Slits 272a and 272b facilitate the folding of flap 275 and its retention in the tucked-in configuration by second and fifth panels 220 and 250, respectively, as discussed below. Seventh panel 270 forms the floor for the drawer portion 200 when the blank is folded, as explained below.

Elongated reinforcement strip 280 extends angularly from body portion 241, reinforcement strip 280 being connected to an edge of body portion 241 along fold line 285. Reinforcement strip 280 includes angled body 286, which is oriented at an angle A with respect to fold line 285, wherein angle A preferably ranges from about 40° to 50°, and more preferentially is about 45°. Tab 282 is foldably connected to angled body 286 along fold line 281 and includes a semicircular insertion portion 283. Insertion portion 283 is adapted to engage slit 264 in the sixth panel 260 and reinforces the corner of the drawer portion 200 adjacent a portal through which the suture packages are withdrawn by providing a catercornered support strut.

Figure 8:
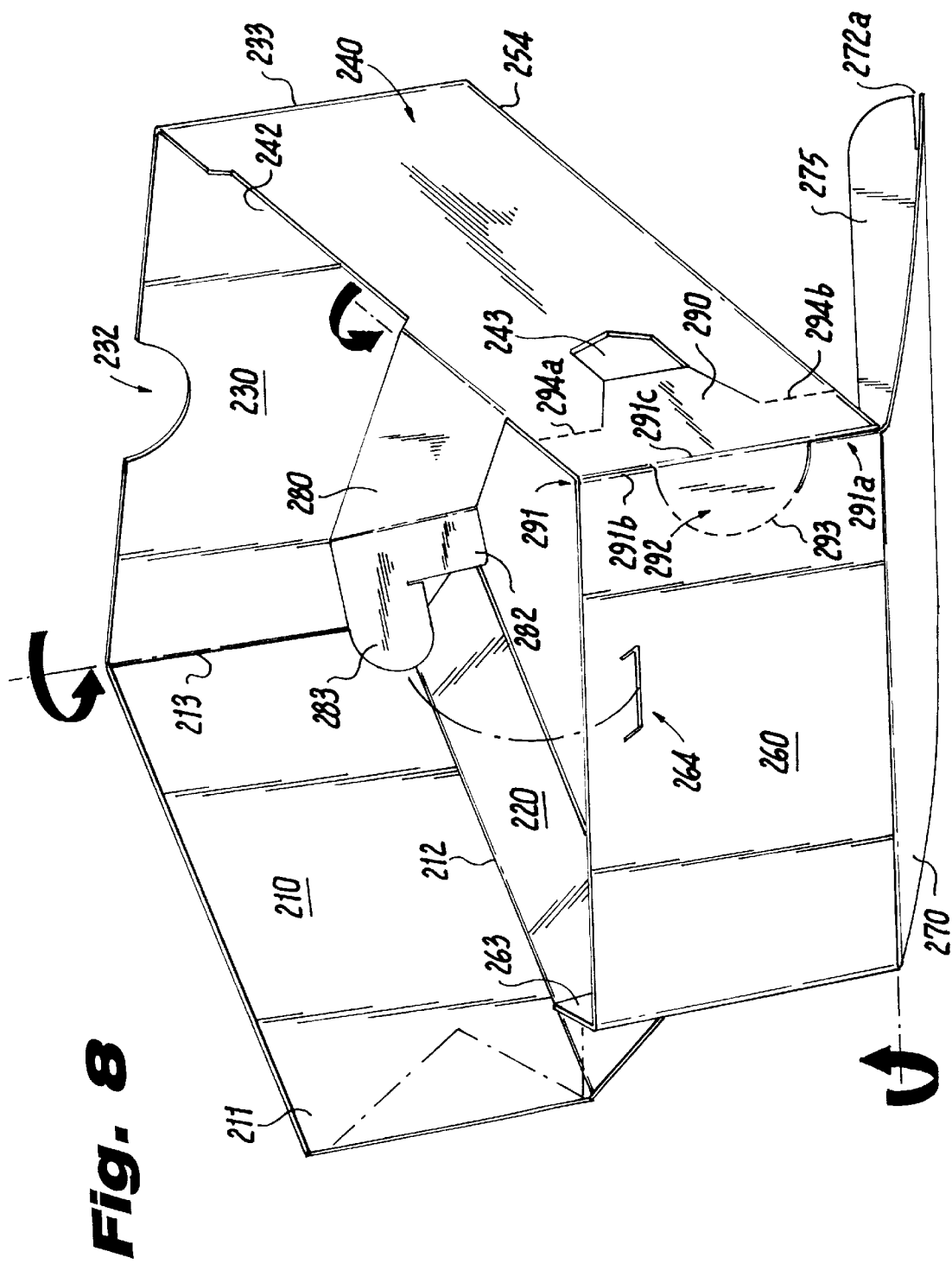
FIG. 8 is a perspective view showing the folding and assembly of the blank of FIG. 7 to form the drawer.

Referring to FIG. 8, the folding assembly of the drawer portion 200 is illustrated. First, third, fourth, and sixth panels 210, 230, 240, and 260, respectively, are folded around along fold lines 213, 233, and 291 to form the sides of the drawer portion 200.

Second and fifth panels 220 and 250, respectively, are then folded up and in along fold lines 212 and 254, respectively. Seventh panel 270, which forms the floor of the drawer portion 200, is then folded up with flap 275 being inserted in the space between body portion 231 and angled edges 223 and 253 of panels 220 and 250, respectively. Lateral offset portions 222 and 252 engage slots 272b and 212a, respectively, thereby retaining the flap 275. Reinforcement strip 280 is then folded at fold line 285 across the top of drawer portion 200, and the insertion portion 283 of tab 282 is inserted into slit 264 of the sixth panel 260. The catercornered orientation of reinforcement strip 280 provides additional structural support to drawer portion 200 at the corner formed between the fourth and sixth panels 240 and 260, respectively. As mentioned above, flap 263 can be bonded to the inside surface of the first panel 210, for example, by use of a suitable adhesive.

As can be seen from FIGS. 3, 4, and 9 and suture package dispenser 10 is a container for holding a plurality of suture packages 50 in a stacked array, the suture packages 50 being of generally planar, rectangular configuration, stacked parallel to each other. The suture package dispenser 10 is characterized by a generally planar first side wall 11 and a generally planar second side wall 12, side walls 11 and 12 being adjacent and substantially perpendicular to each other, and a side wall 13 which constitutes a top panel when the suture dispenser is positioned horizontally on a support surface, as shown in FIG. 4. The first side wall 11 is defined by wall 120 of the outer casing (FIG. 5) in conjunction with panel 240 of the drawer portion (FIGS. 7, 8). Side wall 12 is defined by panel 230 of the drawer portion (FIGS. 7, 8) and spacer portion 172. Side wall 13 is defined by wall 110 (FIGS. 5, 6), and is substantially perpendicular to side walls 11 and 12. The planes of the individual suture packages are oriented perpendicular to the first and third side walls 11 and 13, and parallel to the second side wall 12.

Suture package dispenser 10 includes two access portals through which the suture packages can be individually withdrawn. A first portal 14 is located at the bottom of the first side wall 11 when the suture packages dispenser 10 is positioned vertically as shown in FIG. 3.

Figure 12:
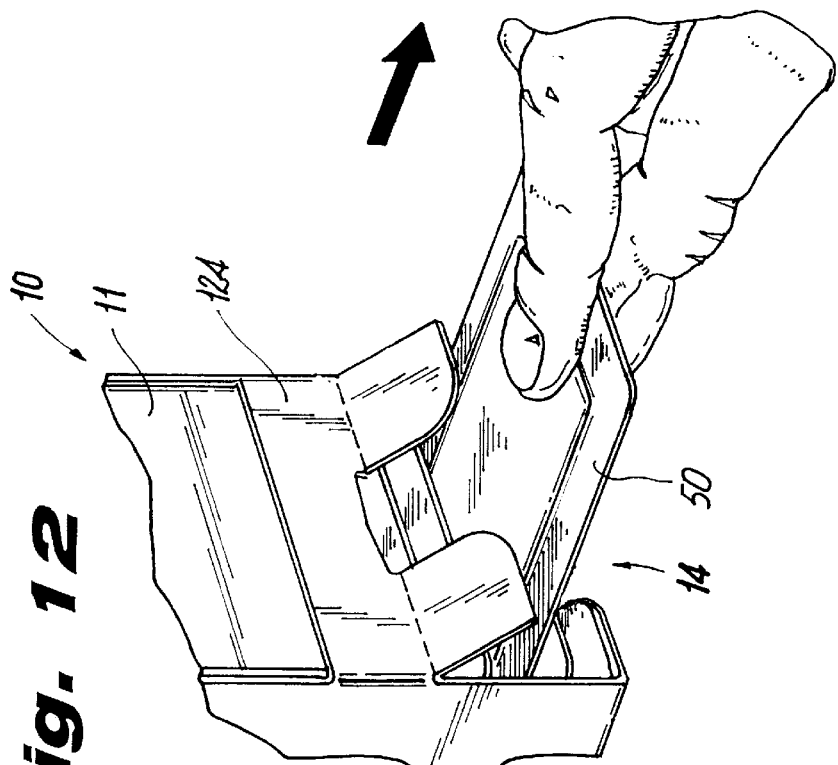
FIG. 12 is a perspective view illustrating the dispensing of a suture package.
Figure 11:
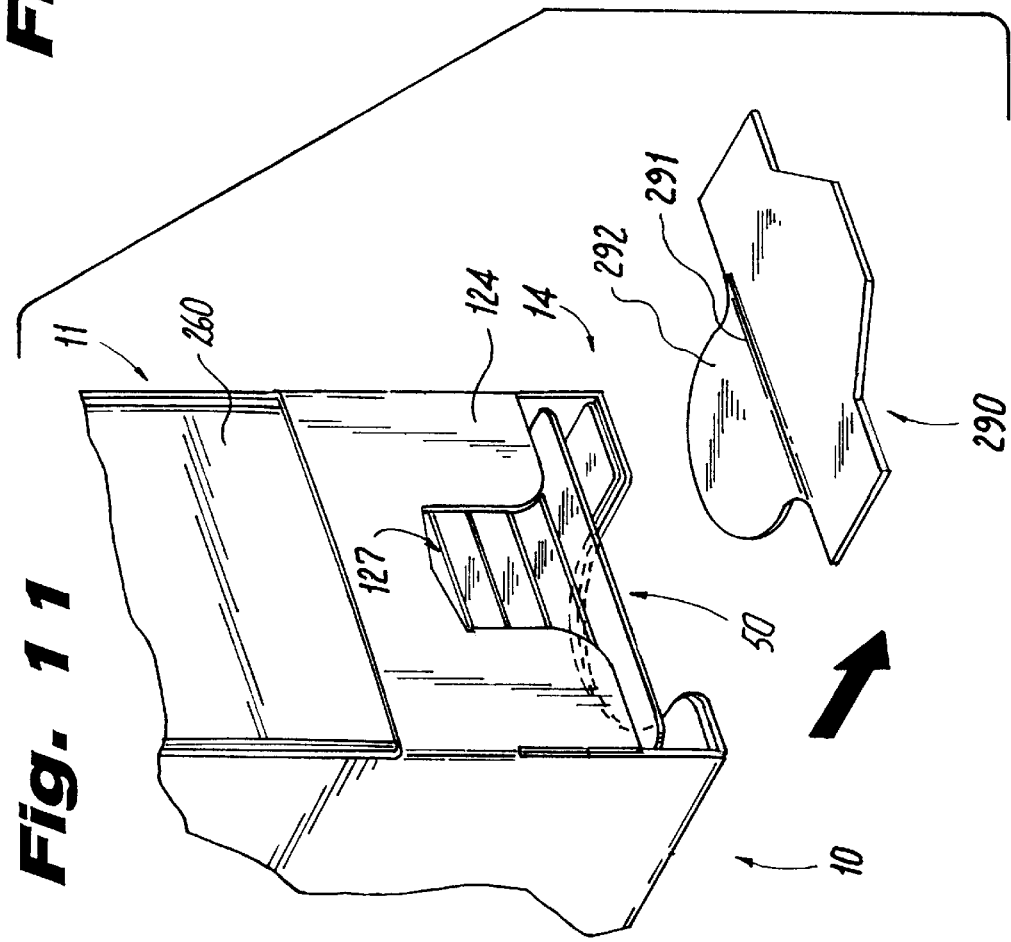
FIG. 11 is a perspective view illustrating the removal of the retainer tab.

Referring to FIGS. 11 and 12, removable retainer piece 290 is initially folded over to at least partially close the first portal 14. To withdraw a suture package from the first portal 14 the user detaches retainer piece 290, thereby allowing retrieval of a suture package 50.

As can be seen in FIG. 12, the suture packages 50 are individually withdrawn through the first portal 14 in a line of direction perpendicular to the first side wall 11 and parallel to both the second side wall 12 and the third side wall 13, as in the U.S. preferred mode of dispensing.

Figure 1:
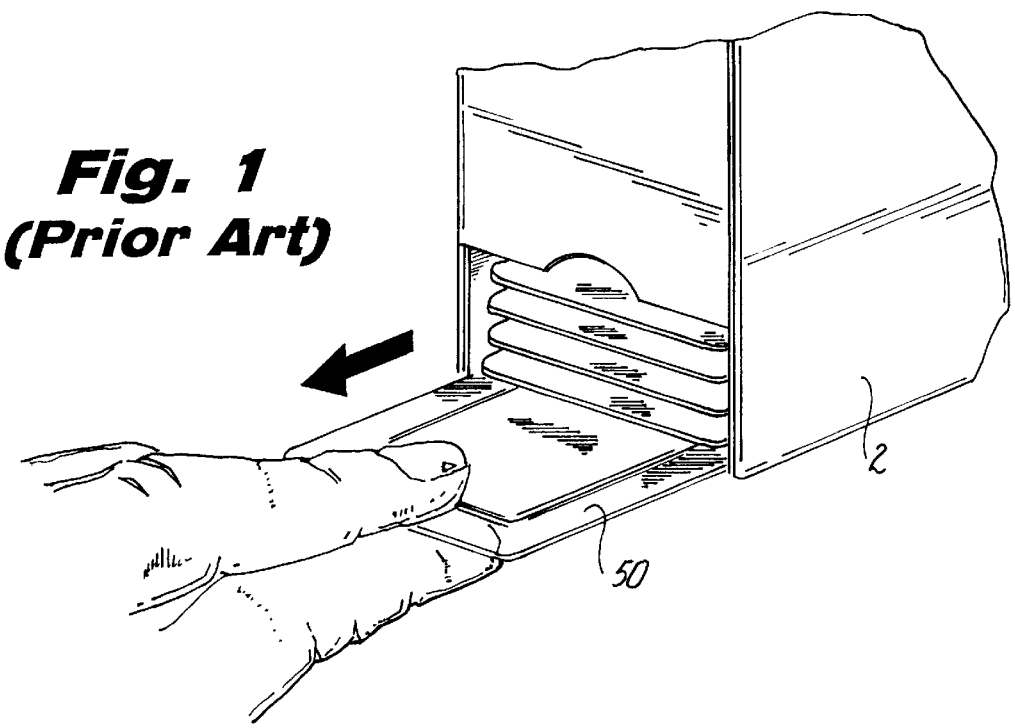
FIGS. 1 and 2 illustrate prior art methods of dispensing suture packages from box containers.
Figure 2:
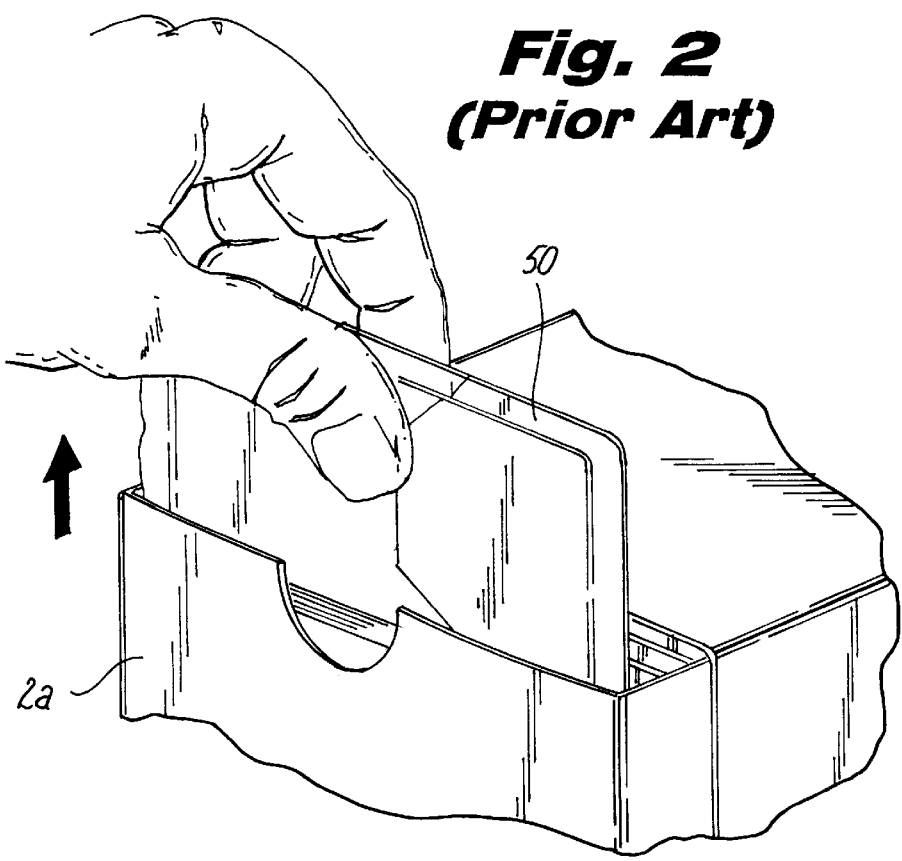

Referring to FIG. 4 a second portal 15 is defined by side walls 12 and 13. When the drawer portion 200 is fully inserted into the outer casing 100, the second portal 15 is in a closed configuration. When the drawer portion 200 is at least partially withdrawn from the outer casing 100 the second portal 15 is open and a suture package 50 can be removed as in the European preferred mode. See e.g., FIG. 2 which illustrates the European preferred mode of dispensing.

As can be seen, the suture package is removed from the second portal in a line of direction perpendicular to third side wall 13, but parallel to both the first side wall 11 and the second side wall 12, although, as mentioned above, the planes of the suture packages are perpendicular to the first side wall 11 and parallel to the second side wall 12.

Referring to FIG. 10, conventional suture package dispenser boxes 2 are shown oriented vertically for use in the U.S. preferred mode of dispensing. A typical U.S. dispenser box has a depth A, of about 5.4 inches. However, the width of the European style box is typically about 4.7 inches (i.e., the length of panel 230 between fold lines 213 and 233, FIG. 7).

The outer casing 100 is adapted to correspond in dimensions to U.S. prior art suture package dispensers 2 so that suture package dispenser box 10 can be shelved alone or side by side with the conventional boxes 2 on a standardized U.S. display or storage rack 5 to present a uniform array of dispenser boxes flush with the front of the shelving. Both the prior art suture package dispensers 2 and the outer casing 100 of the suture dispenser 10 are characterized by a depth dimension A. However, the drawer portion 200 is characterized by a dimension L which is less than A. It is this dimension L, that corresponds to the preferred European width for a suture dispensing box (i.e. about 4.7 inches). Spacer walls 160 and 170 provide an interior wall formed by body portions 161 and 171, which is spaced apart from exterior panel 141 by a distance D equal to the width of spacer portions 162 and 172. Width D is chosen such that the dimensions of the drawer portion 200 are accommodated within the outer casing 100, as previously explained. Most preferably, with respect to FIG. 10, dimension A is about 5.4 inches, spacer width D is about 0.7 inches, height H is about 5.6 inches and box width W is about 2.5 inches. Therefore, the exterior dimensions of the U.S. preferred suture dispensing box is about 2.5×5.6×5.4 inches, while the European suture package dispenser drawer is about 2.5×5.6×4.7 inches (± about 0.5 inches in each dimension).

The suture package dispenser 10 described herein is substantially more efficient than prior known suture package dispenser boxes in that it advantageously allows a single dispenser box to be used in both U.S. and European modes of operation, thereby providing economy of manufacture, and the advantages of unified labeling and inventory systems.

It will be understood that various modifications may be made to the embodiments described herein. Therefore the above description should not be construed as limiting, but merely as exemplifications of preferred embodiments. Those skilled in the art will envision other modifications within the scope and spirit of the claims appended hereto.

What is claimed is:

1. A container for storing and dispensing suture packages, which comprises:

an outer casing defining an interior space; and a drawer portion removably inserted into the interior space of the outer casing, the drawer portion having a floor portion and four panels defining a suture package storage compartment, the drawer portion having a support strip extending catercornered between two adjacent panels of said four panels, wherein said drawer portion contains indicia on an exterior surface of at least one of said panels, and said outer casing includes a window opening such that the indicia are visible through said window opening in the outer casing.

2. The container of claim 1 further including first and second access portals to permit withdrawal of suture packages from the suture package storage compartment.

3. The container of claim 2 wherein the catercornered support strip is positioned in the vicinity of the first access portal.

4. The container of claim 1 wherein the support strip is foldably connected to one of the two adjacent panels, the support strip having a tab received into a corresponding slot in the other of the two adjacent panels.

5. A suture package dispenser comprising:

a plurality of suture packages;

a container for holding the plurality of suture packages in a stacked array, the suture packages being of generally planar configuration and stacked such that the planes of the packages are parallel to each other;

the container having first and second adjacent sides, the first side generally defining a first plane and the second side generally defining a second plane, wherein the individual suture package planes are oriented perpendicular to the first plane and parallel to the second plane; and, the container having first and second access portals for withdrawal of the suture packages from the stacked array, the first access portal permitting the suture packages to be withdrawn from the container in a line of direction perpendicular to the first plane and parallel to the second plane, and the second access portal permitting the sutures to be withdrawn from the container in a direction parallel to both the first and second planes, wherein the container includes a catercornered support strip in the vicinity of the first access portal;

wherein the container includes an outer casing and a drawer portion slidably disposed within the outer casing, wherein the catercornered support strip extends from a first panel of the drawer portion to a second panel of the drawer portion, and wherein said first panel includes indicia on an exterior surface and the outer casing includes a window opening such that the indicia on the first panel are visible through said window opening in the outer casing.

6. The suture package dispenser of claim 5 wherein the drawer portion has a storage space for holding the stacked array of suture packages.

7. The suture package dispenser of claim 7 wherein the first access portal is positioned on the first side of the container and is at least partially defined by corresponding openings in the drawer portion and the outer casing.

8. The suture package dispenser of claim 5 wherein the container is fabricated from a material selected from the group consisting of paperboard, and plastic sheet.

9. The suture package dispenser of claim 5 wherein the second panel of the drawer portion includes indicia on an exterior surface and the outer casing includes a second window opening for viewing the indicia on the second panel.

10. A suture package dispenser comprising:

a plurality of suture packages;

a container for holding the plurality of suture packages in a stacked array, the suture packages being of generally planar configuration and stacked such that the planes of the packages are parallel to each other, the container having first and second adjacent sides, the first side generally defining a first plane and the second side generally defining a second plane, wherein the individual suture package planes are oriented perpendicular to the first plane and parallel to the second plane; and the container having first and second access portals for withdrawal of the suture packages from the stacked array, the first access portal permitting the suture packages to be withdrawn from the container in a line of direction perpendicular to the first plane and parallel to the second plane, and the second access portal permitting the sutures to be withdrawn from the container in a direction parallel to both the first and second planes, wherein the container includes a catercornered support strip in the vicinity of the first access portal, wherein the container includes an outer casing and a drawer portion slidably disposed within the outer casing, wherein the catercornered support strip extends from a first panel of the drawer portion to a second panel of the drawer portion, wherein the drawer portion has a storage space for holding the stacked array of suture packages, wherein the first access portal is positioned on the first side of the container and is at least partially defined by corresponding openings in the drawer portion and the outer casing, and wherein the opening in the drawer portion is at least partially formed by removal of a tab which is removably attached to the drawer portion at a corner formed between the first and second panels of the drawer portion.

11. The suture package dispenser of claim 10, wherein the second side of the container is defined by an end panel of the drawer portion, the outer casing having a first side wall which is adjacent and substantially perpendicular to the first and second sides of the container, and the second portal is at least partially defined by the end of the drawer portion and the first side wall of the outer casing, the second portal being in an open configuration when the drawer portion is at least partially withdrawn from the outer casing and in a closed configuration when the drawer portion is fully disposed within the outer casing.

12. The suture package dispenser of claim 9 further including first and second access portals for withdrawal of the suture packages, the first access portal permitting the suture packages to be withdrawn from the dispenser in a linear direction perpendicular to the second side of the outer casing, and the second access portal permitting withdrawal of the suture packages in a line of direction perpendicular to the first side of the outer casing.

13. The suture package dispenser of claim 12 wherein the catercornered reinforcement strip is positioned in the vicinity of the first access portal.

14. The suture package dispenser of claim 13 wherein the catercornered reinforcement strip is foldably connected to the fourth panel and includes a tab received into a corresponding slot in the sixth panel.

15. A suture package dispenser comprising:
 a plurality of suture packages;
 a container for holding the plurality of suture packages in a stacked array, the suture packages being of generally planar configuration and stacked such that the planes of the packages are parallel to each other,
 the container having first and second adjacent sides, the first side generally defining a first plane and the second side generally defining a second plane, wherein the individual suture package planes are oriented perpendicular to the first plane and parallel to the second plane, and,
 the container having first and second access portals for withdrawal of the suture packages from the stacked array, the first access portal permitting the suture packages to be withdrawn from the container in a line of direction perpendicular to the first plane and parallel to the second plane, and the second access portal permitting the sutures to be withdrawn from the container in a direction parallel to both the first and second planes, wherein the container includes a catercornered support strip in the vicinity of the first access portal, wherein the container includes an outer casing and a drawer portion slidably disposed within the outer casing, wherein the catercornered support strip extends from a first panel of the drawer portion to a second panel of the drawer portion, and wherein the drawer portion has at least one side dimension which is less than a corresponding side dimension of the outer casing, and the outer casing includes at least one spacer wall spaced apart from an exterior wall of the outer casing by a distance substantially equal to the difference between the corresponding side dimensions of the outer casing and drawer portion, and which is oriented parallel to said first plane.

16. A suture package dispenser comprising:
a) an outer casing which includes a first wall, a second wall foldably connected to the first wall along an edge of the second wall, a third wall foldably connected to the second wall on an edge of the second wall opposite to the edge at which the first wall is foldably connected, a fourth wall foldably connected to the third wall along an edge of the third wall opposite to that at which the second wall is connected, and a fifth wall foldably connected to the third wall; said first, second third, fourth and fifth walls forming at least a partial enclosure defining an interior space and having an open end; and
b) a drawer portion slidably disposed within the interior space of the outer casing and at least partially withdrawable through the open end of the outer casing, the drawer portion including first, second, third, fourth, fifth, sixth, and seventh panels, the second and third panels being foldably connected to the first panel along respective adjacent edges of the first panel, the fourth panel being foldably connected to the third panel along an edge of the third panel opposite to the edge at which the first panel is foldably connected, the fifth and sixth panels being foldably connected to the fourth panel along respective adjacent edges of the fourth panel, and the fourth and seventh panels being foldably connected to the sixth panel along respective adjacent edges of the sixth panel, the first, second, third, fourth, fifth, sixth, and seventh panels being folded to form a storage space for suture packages, wherein the drawer portion further includes a reinforcement strip extending at an angle from the sixth panel to the second panel to form a catercornered reinforcement between the fourth and sixth panels.

17. The suture package dispenser of claim 16 wherein the second wall and the fifth wall of the outer casing each have a window.

18. The suture package dispenser of claim 16 wherein the first wall includes a tab and the fifth wall includes a slot into which the tab is inserted.

19. The suture package dispenser of claim 16 wherein the sixth panel and third panel of the drawer portion are foldably attached to opposite edges of the fourth panel of the drawer portion.

20. The suture package dispenser of claim 16 wherein said outer casing and drawer portion are fabricated from a material selected from the group consisting of paperboard and plastic sheet.

21. The suture package dispenser of claim 16 further including a plurality of substantially planar suture packages stacked in an array such that the suture packages are parallel to each other and parallel to third and sixth panels of the drawer portion.

* * * * *